United States Patent
Fassian et al.

(10) Patent No.: US 6,320,199 B1
(45) Date of Patent: Nov. 20, 2001

(54) PROCESS FOR IMPROVING THE RELIABILITY OF OPERATION OF OPTICAL GAS SENSORS

(75) Inventors: Bernd Fassian, Lübeck; Günter Wahlbrink, Upn Knust; Robert Kessel, Bad Oldesloe, all of (DE)

(73) Assignee: Dräger Sicherheitstechnik GmbH (DE)

( * ) Notice: Subject to any disclaimer, the term of this patent is extended or adjusted under 35 U.S.C. 154(b) by 0 days.

(21) Appl. No.: 09/568,346

(22) Filed: May 10, 2000

(30) Foreign Application Priority Data

Aug. 12, 1999 (DE) .............................. 199 38 280

(51) Int. Cl.$^7$ .................................. G01N 21/00
(52) U.S. Cl. ................... 250/573; 250/221; 250/559.39
(58) Field of Search .............................. 250/554, 559.03, 250/559.06, 559.11, 559.2, 559.39, 573, 336.1, 338.1, 338.5, 340, 343, 345, 221; 356/432, 436, 437

(56) References Cited

U.S. PATENT DOCUMENTS 5,969,623 * 10/1999 Fleury et al. ..................... 340/632
6,096,560 * 8/2000 Scripca et al. ..................... 436/164

FOREIGN PATENT DOCUMENTS 197 13 928
C1 4/1998 (DE) .

* cited by examiner

Primary Examiner—David V. Bruce
Assistant Examiner—Hoon K. Song
(74) Attorney, Agent, or Firm—McGlew and Tuttle, P.C.

(57) ABSTRACT

A process is provided for improving the reliability of operation of optical gas sensors with at least one radiation source and with at least one radiation detector. By comparing and evaluating the measured signals (18) (D) sent by the radiation detector, of which there is at least one, with first, second and third stored reference values ($D_1$, $D_2$, K), it is achieved, on the one band, that in the case of toxic gas concentrations or of gas concentrations that are critical because of explosion hazard, second measured values (15) continue to be sent for the protection of the user corresponding to the range between the reference values $D_1$ and $D_2$ when the third reference value (K) is exceeded. On the other hand, at least first warning signals (16) are sent by the gas sensor to warn that a preset degree of contamination has been reached in order for maintenance or cleaning of the gas sensor to be performed or in order for the gas sensor to be replaced with a new gas sensor shortly.

10 Claims, 2 Drawing Sheets

PROCESS FOR IMPROVING THE RELIABILITY OF OPERATION OF OPTICAL GAS SENSORS

FIELD OF THE INVENTION

The present invention pertains to a process for improving the reliability of operation of optical gas sensors.

BACKGROUND OF THE INVENTION

Optical gas sensors usually have one or more radiation sources, which emit suitable radiation over a measured section, wherein the resulting measuring beams pass through the measured section containing the gas to be measured once or several times, and the intensity of the measuring beams weakened by the optical absorption of the gas to be measured is measured by means of one or more radiation detectors. The residual, measured radiation intensity of a gas-specific wavelength or gas-specific wavelengths is an indicator of the concentration of the measured gas.

Such a measuring device is described, e.g., in DE 197 13 928 C1.

The infrared absorption is characteristic for the measurement of the concentrations of many gases, e.g., hydrocarbons (e.g., methane), and it is therefore particularly preferred for the measurement.

A problem arises in the prior-art optical gas sensors from the fact that the optical measured section must be as readily accessible as possible to the gas to be measured in order for a measured signal representative of the current gas concentration at the site of the measurement to be able to be obtained possibly without a time delay.

Since the measured section is usually limited by optical elements, such as windows, mirrors or lenses or is provided with such elements, these elements are also exposed to interfering environmental effects, e.g., rain, snow, dust, aerosols or contaminants in the same manner at the site of the measurement, besides the gases to be measured. These environmental effects lead to disturbances or weakening of the measuring beam and ultimately of the measured signal sent by the radiation detectors.

When the measuring beam is weakened beyond a certain extent, the concentration of the gas to be measured cannot be measured any longer, so that the measuring unit with the radiation detectors will send more or less abruptly an interference signal in this case, especially an electric interference signal in the form of a constant current intensity.

SUMMARY AND OBJECTS OF THE INVENTION

The object of the present invention is to provide a process for optical gas sensors that increases the reliability of operation in the case of increasing interferences of the measuring beam due to environmental effects.

According to the invention, a process is provided for improving the reliability of operation of optical gas sensors with at least one radiation source and at least one radiation detector. The measured signals sent by the radiation detector, of which there is at least one, are first compared with a first stored reference value, so that when the first stored reference value ($D_1$) is exceeded by the measured signals (D) sent by the radiation detector the corresponding measured values are sent by the gas sensor, and when the first stored reference value ($D_1$) does not exceed the measured signals (D) sent by the radiation detector, the measured signals (D) are compared with a second stored reference value ($D_2$), so that when the second stored reference value ($D_2$) is exceeded by the measured signals (D) sent by the radiation detector, the measured signals are compared with a third stored reference value (K), and when the third stored reference value (K) does not exceed the measured signals (D) sent by the radiation detector, the corresponding measured values are sent by the gas sensor, and when the third stored reference value (K) is exceeded by the measured signals (D) sent by the radiation detector, the first warning signals are sent by the gas sensor and, when the second stored reference value ($D_2$) is not exceeded by the measured signals (D) sent by the radiation detector, the second warning signals are sent by the gas sensor.

The process may also compare the measured signals sent by the radiation detector with the stored reference value or stored reference values ($D_1$, $D_2$, K) at preset, adjustable time intervals.

The warning signals may be sent by means of a constant current, a digital signal, an optical display and/or by means of an acoustic warning means. The first and second warning signals and/or the third warning signals may be sent by the gas sensor in the form of a constant current. The first and second warning signals and/or the measured values may be interrupted at preset, adjustable time intervals.

The third stored reference value (K) preferably corresponds to a characteristic concentration critical for the gas to be measured, especially to the concentration of the gas that is the maximum allowable concentration at the workplace or to the concentration of the gas in a gas mixture, which concentration is critical for an explosion limit. When the second stored reference value ($D_2$) is overshot and the third stored reference value (K) is at the same time not exceeded by the measured signals (D) sent by the radiation detector, additional third warning signals are preferably sent by the gas sensor.

One essential advantage of the process according to the present invention is, especially in the case of toxic or explosive gases to be measured, that the readiness of the gas sensor to measure, which may be vitally important, is increased, combined with the timely warning of a limited operating state, during which the user or users of the gas sensor are protected from toxic damage and machines and units located in the environment are protected from explosion damage, because critical gas concentrations continue to be measured and displayed.

It shall be mentioned in connection with the design of the process according to the present invention that it is described in the patent claims and in the description of the exemplary embodiment such that the measured signals increase with increasing degree of contamination, so that defined stored reference values for the degree of contamination are reached quasi from below and are optionally exceeded with increasing degree of contamination.

The optical measured signals received by the radiation detector, of which there is at least one, do, of course, become weaker in practice with increasing degree of contamination, so that the process according to the present invention should be considered in this case to be complementary and equivalent to the text of the patent claims as written, i.e., e.g., such that when the measured signal drops below the first stored reference value according to this text, the measured signals are compared with a second stored reference value, so that when the measured signals sent by the radiation detector, of which there is at least one, also drops below the second stored reference value, warning signals are sent by the gas sensor. However, when the measured signal drops only below the first stored reference value, but not below the second stored reference value, it is compared with a third stored reference value, which is, in general, an indicator of a critical gas concentration: depending on whether or not this indicator of a critical gas concentration is exceeded, measured values are sent (for a critical gas concentration when the measured signal exceeds the indicator) or first warning signals are sent (when the indicator for a critical gas concentration is not exceeded).

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENT

Figure 1:
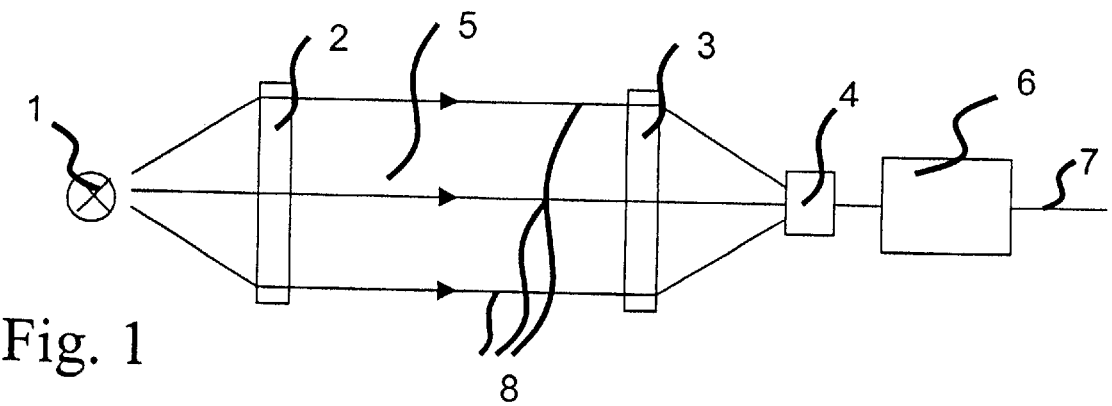
FIG. 1 is a schematic view showing a design of a gas sensor according to the invention.

Referring to the drawings in particular, the arrangement of an optical gas sensor operating preferably in the infrared wavelength range is schematically shown in FIG. 1. Such a gas sensor is used to measure the concentration of gases, wherein the absorption of the measuring beam 8 is evaluated at least at one wavelength characteristic of the gas to be measured.

Figure 2:
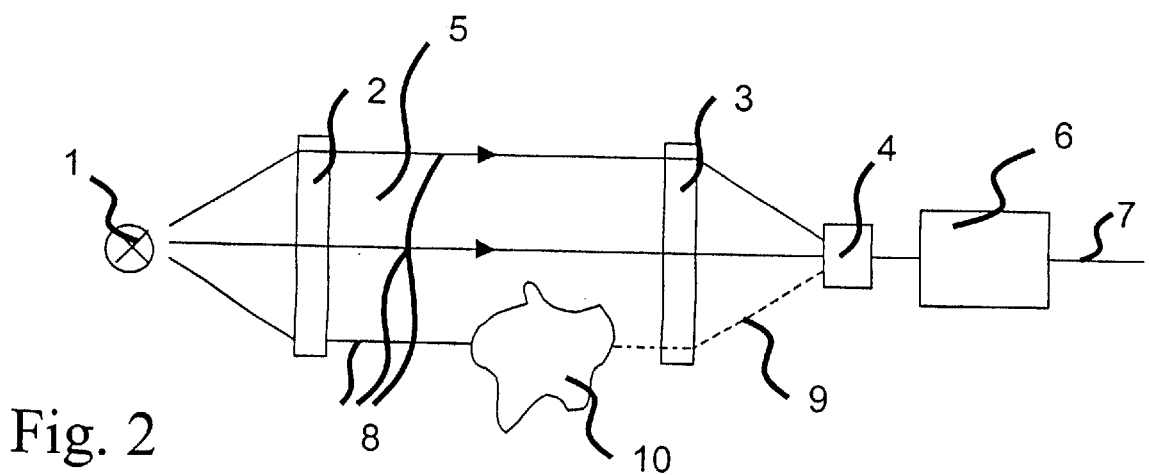
FIG. 2 is another schematic view showing a design of a gas sensor according to the invention.
Figure 3:
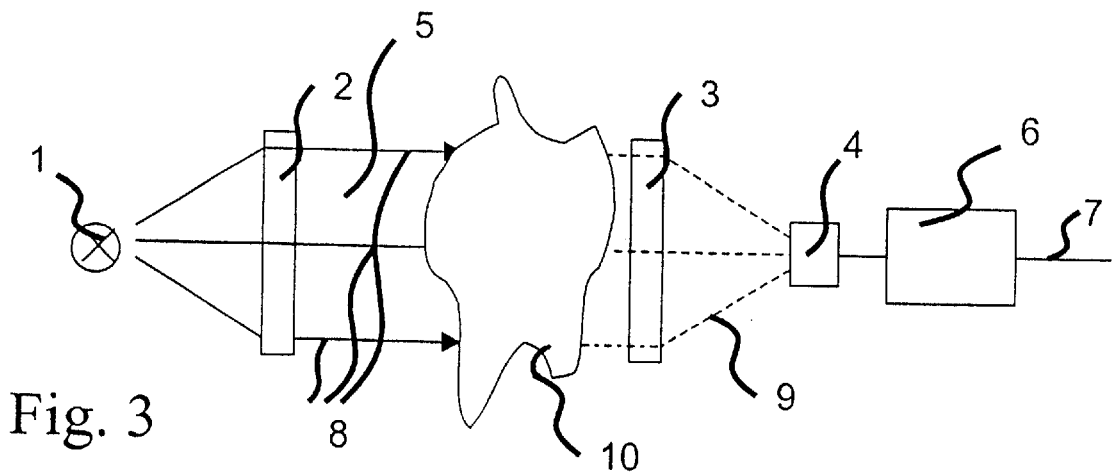
FIG. 3 is another schematic view showing a design of a gas sensor according to the invention.

The measuring beams 8 originating from the radiation source 1 pass through an optical window 2 and a measured section 5 with the gas to be measured, which is limited by a second window 3 (on the right in FIGS. 1 through 3). The measuring beams 8 finally reach a radiation detector 4, of which there is at least one. The measured signals of the radiation detector 4 are processed in the evaluating unit 6 and are sent as measured values 7, especially as current values. If contamination 10 now enters the measured section 5 or comes to the optical windows 2, 3 according to FIG. 2, a part 9 of the measuring beams 8 emitted by the radiation source 1, which part is indicated by broken line, is weakened. FIG. 3 shows the case in which the contamination 10 occupies the entire measured section 5 or completely covers the optical windows 2, 3, so that the radiation detector 4 no longer receives any radiation from the radiation source 1 because the part 9 indicated by broken line occupies the entire radiation cross section behind the contamination 10. A comparison of FIGS. 1 and 2 shows clearly that depending on the degree of contamination, the weakening of the signal is gradual and is generally time-dependent.

Figure 4:
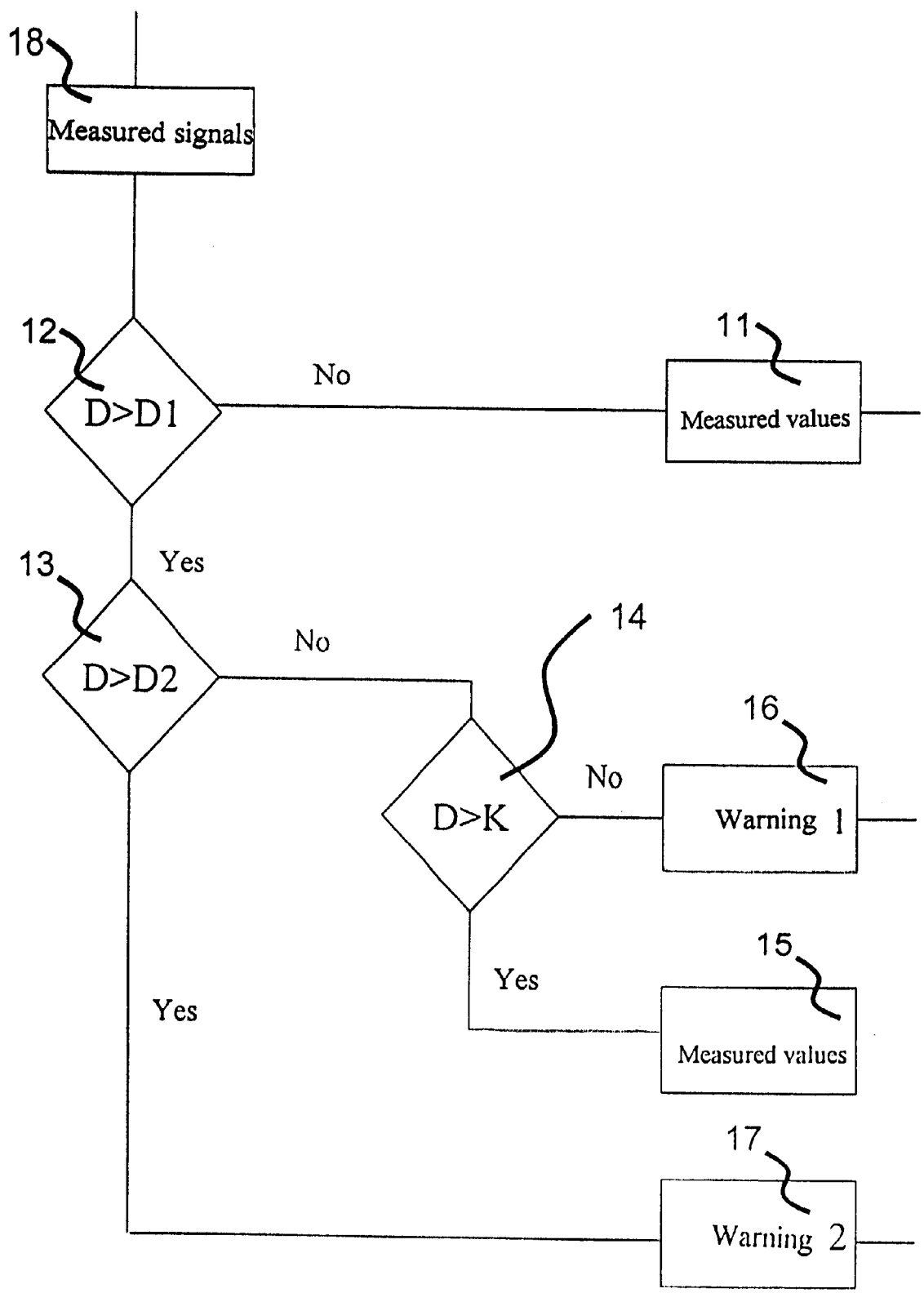
FIG. 4 is a diagram showing the decision structure of the evaluating unit of the gas sensor according to FIGS. 1 through 3.

To explain the process according to the present invention, FIG. 4 shows the decision structure of the evaluating unit 6, which is designed especially as an electronic unit.

If the measured section 5 contains no contamination 10 or only a slight contamination 10, first measured values 11 corresponding to the respective measured signals D and 18 are sent.

The measured signals D of the radiation detector 4 are picked up by means of a first comparator 12 at periodic intervals in order to determine the current degree of contamination of the gas sensor by comparison with a first stored reference value $D_1$.

If the degree of contamination is greater than that preset level, e.g., a weaker signal than $D_1$, i.e., D<D, a second comparator 13 performs an evaluation to determine whether the current degree of contamination is also greater than a second stored reference level, e.g. the signal value is weaker than $D_2$ for the measured signals D. When the value of the measured signals D $D_2$ do not exceed, measurement of the gas concentration is no longer meaningful, so that second warning signals 17, especially in the form of a constant electric current, are sent.

If the second comparator 13 comes to the result, by comparing the measured signals D with the second stored reference $D_2$, that this second reference value is exceeded, the measured signals D are evaluated by another, third comparator 14 by comparing them with a third stored reference value K.

When the third stored reference value K is not exceeded by the measured signals D, the contamination 10 of the measured section 5 is ignored and second measured values 15 are sent for the protection of the user, e.g., because a concentration of a toxic gas that is the maximum allowable concentration at the workplace is not reached or because a concentration of the gas to be measured, which concentration is not critical for an explosion limit in a gas mixture, is reached.

When the third stored reference value K is exceeded, i.e., when a hazardous gas concentration is present, first warning signals 16 are sent by the gas sensor because a critical degree of contamination of the measured section 5 has been reached.

As an alternative, the third comparator 14 could be omitted in the contamination interval corresponding to the range of values between the reference values $D_1$ and $D_2$ and switching back and forth could be performed at preset, adjustable time intervals between the sending of measured values 15 and the sending of first warning signals 16.

The warning signals 17 warn the user that the operation of the gas sensor is no longer reliable because of the degree of contamination, so that maintenance with cleaning is necessary and a second gas sensor should be put into operation as an alternative to maintain the gas measurement.

At the same time, it is, however, also possible with the process according to the present invention that second measured values 15 are sent for the protection of the user in the case of toxic gas concentrations or of gas concentrations that are critical because of the explosion hazard in a gas mixture corresponding to the range between the reference values $D_1$ and $D_2$ when the third reference value K is exceeded. The first reference value $D_1=D_2$ that is the only relevant reference value so far, i.e., the value beginning from which the measurement and the sending of measured values abruptly ceased, corresponded in practical experiments to a degree of contamination of about 50% to 70%. The second reference value $D_2$ (less than $D_1$) additionally used in the process according to the present invention corresponded to a degree of contamination of about 80% to 90%, so that a marked improvement was achieved compared with the prior-art process, which permitted a measurement only until the reference value $D_1$ was reached.

While specific embodiments of the invention have been shown and described in detail to illustrate the application of the principles of the invention, it will be understood that the invention may be embodied otherwise without departing from such principles.

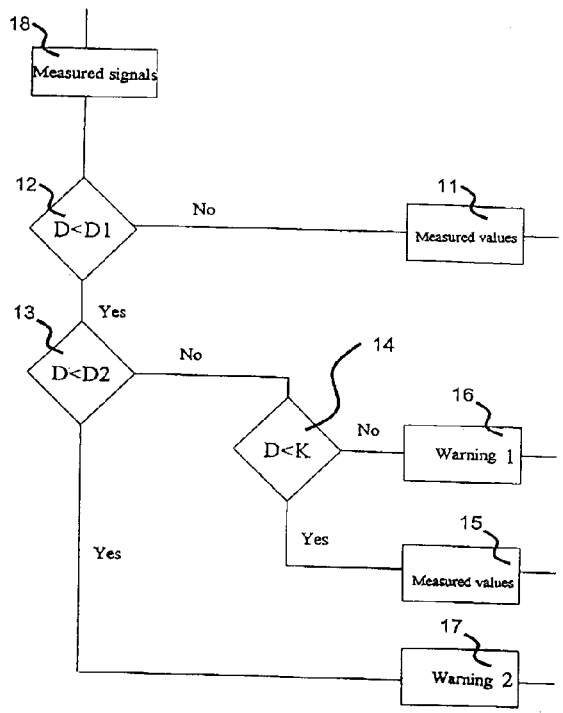

What is claimed is:

1. A process for improving the reliability of operation of optical gas sensors with at least one radiation source and at least one radiation detector, the process comprising the steps of:

comparing the measured signals sent by the radiation detector with a first stored reference value ($D_1$) and when the first stored reference value ($D_1$) is exceeded by the measured signals (D) sent by the radiation detector, corresponding measured values are sent by the gas sensor, and when the first stored reference value ($D_1$) is not exceeded by the measured signals (D) sent by the radiation detector, the measured signals are compared with a second stored reference value ($D_2$) and when the second stored reference value ($D_2$) is exceeded by the measured signals (D) sent by the radiation detector, the measured signals are compared with a third stored reference value (K), and when the third stored reference value (K) is not exceeded by the measured signals (D) sent by the radiation detector, said corresponding measured values are sent by the gas sensor, and when the third stored reference value (K) is exceeded by the measured signals (D) sent by the radiation detector, a first warning signal is sent by the gas sensor and when the second stored reference value ($D_2$) is not exceeded by the measured signals (D) sent by the radiation detector, a second warning signal is sent by the gas sensor.

2. A process in accordance with claim 1, wherein said measured signals (D) sent by said radiation detector, are compared with the stored reference value or stored reference values ($D_1$, $D_2$, K) at preset, adjustable time intervals.

3. A process in accordance with claim 1, wherein said warning signals are sent by means of a constant current, a digital signal, an optical display and/or by means of an acoustic warning means.

4. A process in accordance claim 1, wherein said third stored reference value (K) corresponds to a characteristic concentration critical for the gas to be measured.

5. A process in accordance claim 4, wherein said third stored reference value (K) corresponds to to the concentration of the gas that is the maximum allowable concentration at the workplace or to the concentration of the gas in a gas mixture, which concentration is critical for an explosion limit.

6. The process in accordance with claim 1, wherein when said measured signals are not lower than said second stored reference value ($D_2$) and said third stored reference value (K) is at the same time not exceeded by the measured signals (D) sent by the radiation detector, an additional third warning signal is sent by the gas sensor.

7. The process in accordance claim 6, wherein said first and second warning signals and/or said third warning signal are sent by the gas sensor in the form of a constant current.

8. The process in accordance claim 1, wherein said first and second warning signals are sent by the gas sensor in the form of a constant current.

9. The process in accordance with claim 1, wherein said first and second warning signals and/or said measured values are interrupted at preset, adjustable time intervals.

10. A process for improving the reliability of operation of optical gas sensors with at least one radiation source and at least one radiation detector, the process comprising the steps of:

comparing the measured signals sent by the radiation detector with a first stored reference value and when the first stored reference value is exceeded by the measured signals sent by the radiation detector, sending corresponding measure values;

when the first stored reference value is not exceeded by the measured signals sent by the radiation detector in said step of comparing the measured signals, comparing the measured signals with a second stored reference value;

when the second stored reference value is exceeded by the measured signals sent by the radiation detector in said step of comparing the measured signals with a second stored reference value, comparing the measured signals with a third stored reference value;

when the third stored reference value is not exceeded by the measured signals sent by the radiation detector in said step of comparing the measured signals with a third stored reference value, sending corresponding measured values;

when the third stored reference value is exceeded by the measured signals sent by the radiation detector in said step of comparing the measured signals with a third stored reference value, sending a first warning signal; and when the second stored reference value is not exceeded by the measured signals sent by the radiation detector in said step of comparing the measured signals with a second stored reference value, sending a second warning signal.

* * * * *

UNITED STATES PATENT AND TRADEMARK OFFICE
CERTIFICATE OF CORRECTION

PATENT NO.    : 6,320,199 B1
DATED         : November 20, 2001
INVENTOR(S)   : Bernd Fassian et al.

It is certified that error appears in the above-identified patent and that said Letters Patent is hereby corrected as shown below:

The title page should be deleted and substitute therefore the attached title page as shown on the attached page.

Signed and Sealed this

Ninth Day of September, 2003

JAMES E. ROGAN
*Director of the United States Patent and Trademark Office*

(12) United States Patent
Fassian et al.

(10) Patent No.: US 6,320,199 B1
(45) Date of Patent: Nov. 20, 2001

(54) PROCESS FOR IMPROVING THE RELIABILITY OF OPERATION OF OPTICAL GAS SENSORS

(75) Inventors: Bernd Fassian, Lübeck; Günter Wahlbrink, Upn Knust; Robert Kessel, Bad Oldesloe, all of (DE)

(73) Assignee: Dräger Sicherheitstechnik GmbH (DE)

( * ) Notice: Subject to any disclaimer, the term of this patent is extended or adjusted under 35 U.S.C. 154(b) by 0 days.

(21) Appl. No.: 09/568,346

(22) Filed: May 10, 2000

(30) Foreign Application Priority Data

Aug. 12, 1999 (DE) .............................. 199 38 280

(51) Int. Cl.[7] .................................................. G01N 21/00
(52) U.S. Cl. ...................... 250/573; 250/221; 250/559.39
(58) Field of Search ............................... 250/554, 559.03, 250/559.06, 559.11, 559.2, 559.39, 573, 336.1, 338.1, 338.5, 340, 343, 345, 221; 356/432, 436, 437

(56) References Cited

U.S. PATENT DOCUMENTS 5,969,623 * 10/1999 Fleury et al. ...................... 340/632
6,096,560 * 8/2000 Scripca et al. ...................... 436/164

FOREIGN PATENT DOCUMENTS 197 13 928 C1   4/1998   (DE)

* cited by examiner

Primary Examiner—David V. Bruce
Assistant Examiner—Hoon K. Song
(74) Attorney, Agent, or Firm—McGlew and Tuttle, P.C.

(57) ABSTRACT

A process is provided for improving the reliability of operation of optical gas sensors with at least one radiation source and with at least one radiation detector. By comparing and evaluating the measured signals (18) (D) sent by the radiation detector, of which there is at least one, with first, second and third stored reference values ($D_1$, $D_2$, K), it is achieved, on the one band, that in the case of toxic gas concentrations or of gas concentrations that are critical because of explosion hazard, second measured values (15) continue to be sent for the protection of the user corresponding to the range between the reference values $D_1$ and $D_2$ when the third reference value (K) is exceeded. On the other hand, at least first warning signals (16) are sent by the gas sensor to warn that a preset degree of contamination has been reached in order for maintenance or cleaning of the gas sensor to be performed or in order for the gas sensor to be replaced with a new gas sensor shortly.

10 Claims, 2 Drawing Sheets